US008833953B2

(12) United States Patent
Schmid et al.

(10) Patent No.: US 8,833,953 B2
(45) Date of Patent: Sep. 16, 2014

(54) SURGICAL LAMPS AND RELATED SYSTEMS AND METHODS

(75) Inventors: Michael Schmid, Groebenzell (DE); Mathias Frenzel, Germering (DE); Rudolf Marka, Ismaning (DE); Klaus Thiessen, Puchheim (DE)

(73) Assignee: Trumpf Medizin Systeme GmbH + Co. KG, Saalfeld (DE)

( * ) Notice: Subject to any disclaimer, the term of this patent is extended or adjusted under 35 U.S.C. 154(b) by 483 days.

(21) Appl. No.: 13/246,006

(22) Filed: Sep. 27, 2011

(65) Prior Publication Data

US 2012/0075832 A1    Mar. 29, 2012

(30) Foreign Application Priority Data

Sep. 28, 2010  (EP) .................................... 10181051

(51) Int. Cl.
*A61G 13/00* (2006.01)
*F21V 23/04* (2006.01)
*A61B 19/00* (2006.01)
*H05B 37/02* (2006.01)
*F21V 21/40* (2006.01)
*F21W 131/205* (2006.01)

(52) U.S. Cl.
CPC ......... *A61B 19/5202* (2013.01); *F21V 23/0442* (2013.01); *Y02B 20/44* (2013.01); *F21W 2131/205* (2013.01); *H05B 37/0227* (2013.01); *F21V 21/403* (2013.01); *A61B 2019/5208* (2013.01)
USPC .......................................................... 362/33

(58) Field of Classification Search
CPC .................... F21W 2131/20; F21W 2131/202; F21W 2131/205; F21W 2131/208; F21V 21/403; F21V 23/0442; F21V 23/0471; F21V 23/0478; F21V 23/0485
See application file for complete search history.

(56) References Cited

U.S. PATENT DOCUMENTS

| | | | |
|---|---|---|---|
| 4,656,461 | A | 4/1987 | Morsch et al. |
| 7,311,410 | B2 | 12/2007 | Marka |
| 7,465,065 | B2 | 12/2008 | Marka |
| 7,513,645 | B2 | 4/2009 | Marka et al. |
| 7,614,763 | B2 | 11/2009 | Leibinger et al. |
| 7,746,009 | B2 | 6/2010 | Held et al. |
| 8,292,804 | B2 | 10/2012 | Marka et al. |
| 8,300,906 | B2 | 10/2012 | Voelker |
| 2003/0185009 | A1 | 10/2003 | Walters |
| 2006/0044800 | A1* | 3/2006 | Reime .......................... 362/276 |
| 2008/0311993 | A1 | 12/2008 | Beutler et al. |

(Continued)

FOREIGN PATENT DOCUMENTS

| | | |
|---|---|---|
| DE | 20316755 U1 | 3/2005 |
| EP | 1750052 A1 | 2/2007 |

(Continued)

*Primary Examiner* — Sean Gramling
(74) *Attorney, Agent, or Firm* — Fish & Richardson P.C.

(57) ABSTRACT

A surgical lamp includes a lamp body having at least one light source, wherein at least one bundle of light is emitted from the lamp body, a focusing device disposed in the lamp body for focusing the at least one bundle of light, and an operating device that is directly or indirectly connected to the focusing device and is configured to be covered by a sterilizable cover, where the operating device is configured to detect a predetermined motion sequence of an operator in a contactless manner and control the focusing device as a result of the predetermined motion sequence.

20 Claims, 4 Drawing Sheets

(56) References Cited

U.S. PATENT DOCUMENTS

2009/0318770 A1 12/2009 Marka et al.
2009/0318771 A1 12/2009 Marka et al.
2010/0081887 A1 4/2010 Marka et al.
2012/0075832 A1 3/2012 Schmid et al.

FOREIGN PATENT DOCUMENTS

| EP | 2169965 A1 | 3/2010 |
| FR | 2557711 A1 | 7/1985 |
| GB | 2423378 A * | 8/2006 |
| WO | 2010146446 A1 | 12/2010 |

* cited by examiner

SURGICAL LAMPS AND RELATED SYSTEMS AND METHODS

CROSS-REFERENCE TO RELATED APPLICATION

This application claims priority under 35 U.S.C. §119 to European Patent Application No. 10 181 051.3, filed on Sep. 28, 2010. The contents of the prior application are hereby incorporated by reference in their entirety.

TECHNICAL FIELD

The invention relates to surgical lamps and related systems and methods.

BACKGROUND

During surgeries (e.g., surgeries of human bodies), it is typically necessary that the hands of a surgeon do not become unsterile by touching unsterilized objects.

In order to perform surgeries, proper illumination of the operation site is usually desired by the surgeon. This can be achieved by adjusting different parameters of the surgical lamp used to illuminate the operation site. Therefore, typically, a position and an orientation of the lamp body, the focus of the light rays emitted from the lamp to the operation site, and an intensity of the emitted light rays (i.e., the brightness of the illumination of the operation site) are adjustable. Typically, the surgeon modifies the position and the orientation of the lamp by grabbing the lamp body at a sterile handle cover that is pushed over a handle of the lamp body and physically moving the lamp into the desired position and into the desired orientation. By twisting the sterile handle cover, typically, the focus of the light rays (i.e., the distance of the intersecting point of the emitted light beams from the lamp body) is adjusted.

Adjustment of the brightness is normally not performed by the surgeon, but instead by other operation room personnel that have fewer requirements regarding sterility. Lamp brightness is typically adjusted by non-sterilized devices at the rim of the lamp body, at a carrying system, or at a wall operating unit. However, for this purpose, additional personnel are typically necessary, and obtaining a desired adjustment of the brightness can be more complicated due to the necessary communication between the surgeon and the personnel. Adjusting the brightness of the lamp in this manner can be dangerous, particularly, in critical operative situations and environments.

In order to address the problem, from EP-A-1 750 052, a sterilizable operating member which is attached to a lamp body, in addition to the sterilizable handle, is known, whereby additional functions (e.g., adjusting a light color temperature, adjusting a light distribution, or operating a camera) may be carried out in a sterile manner. However, using this device, an additional operating member is typically necessary due to the possibility of performing adjustments in several modes of operation and the surgeon possibly has to select the desired mode of operation. Therefore, this adjustment of a surgical lamp having only the adjustable functions for brightness and focus can divert the surgeon.

SUMMARY

In some aspects of the invention, a lamp body includes an operating device that can be adjusted in a contactless manner. In this context, in a contactless manner means that the operating device itself, in particular, a sensor of the operating device, is not touched during adjustment. Instead, sterile elements of the lamp body covering the sensor of the operating device may be touched during adjustment.

By using the surgical lamps and methods described herein, operating room personnel (e.g., a surgeon) can adjust the brightness and the focus of a surgical lamp without compromising the sterility of the operating environment (e.g., the operation site or wound, the surgeon's hands, or other operating room equipment).

Additionally, the orientation of a surgical lamp can be altered under sterile conditions without inadvertently affecting the focus of light emitted by the surgical lamp.

The details of one or more embodiments of the invention are set forth in the accompanying drawings and the description below. Other aspects, features, and advantages of the invention will be apparent from the description and drawings, and from the claims.

DETAILED DESCRIPTION

Figure 1:
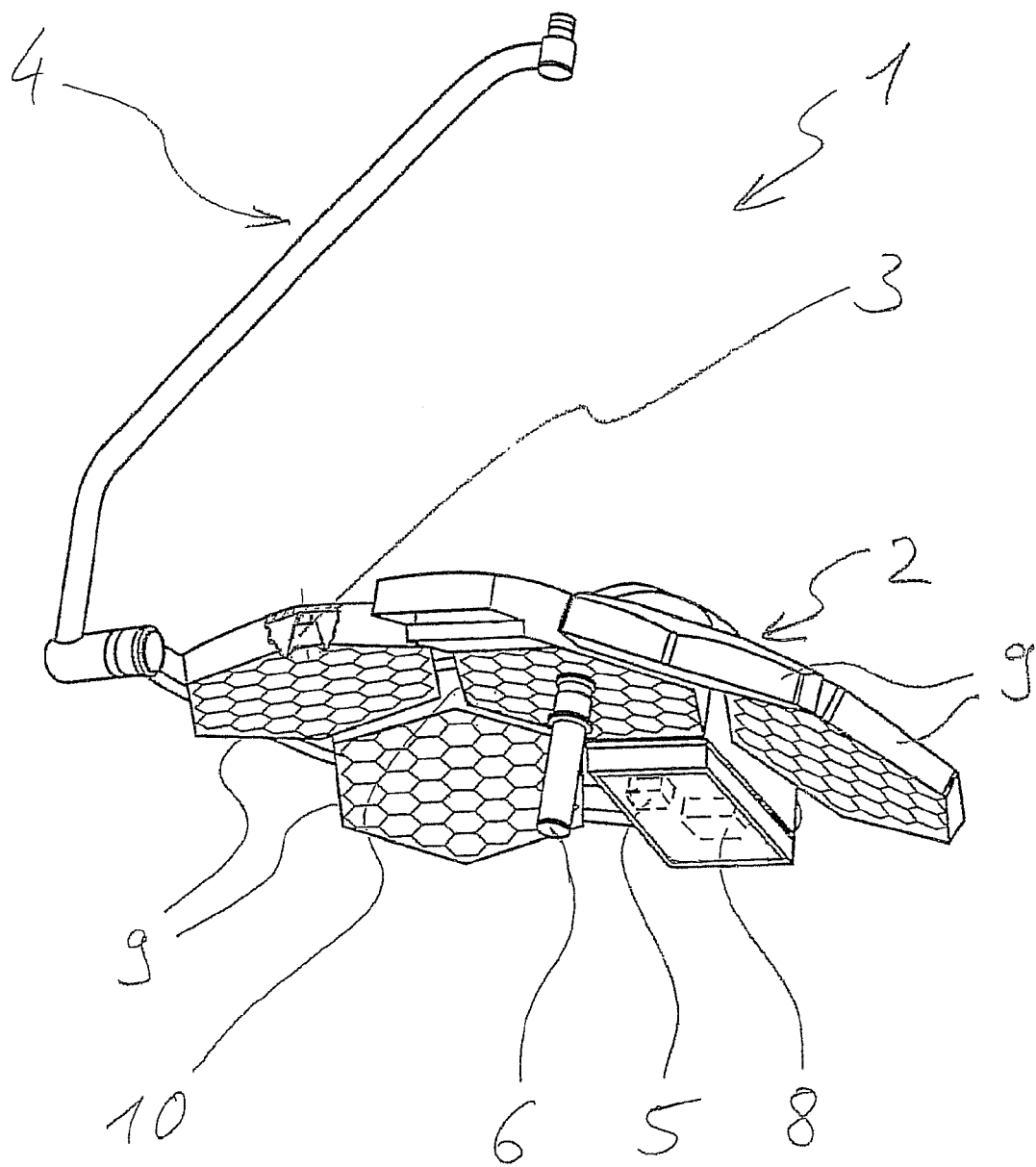
FIG. 1 is a perspective illustration of a surgical lamp.

FIG. 1 shows a surgical lamp 1 that includes a lamp body 2. The lamp body 2 is connected to a structure (e.g., a room ceiling, a mobile stand, or similar suitable structure) by a suspension device 4 of which only a lower portion is shown. The suspension device 4 includes a gimbal-type suspension so that the lamp body 2 can be positioned in a desired position and in a desired orientation within a determined movement radius of the suspension device 4.

The lamp body 2 includes four edge modules 9 and a central module 10. The edge modules 9 are pivotably attached to the central module 10. Alternatively, another number of modules or a different arrangement of the modules can be provided. In some embodiments, the surgical lamp 1 can be provided with multiple single spotlights to create a dissolved light system or it can be constructed as a large mirror lamp. Furthermore, pivotable modules or pivotable spotlights can be provided within a housing of a lamp body.

The edge modules 9 and the central module 10 respectively include a plurality of light sources 3 that are formed by LEDs with a lens. The light sources 3 each emit a bundle of light. In some embodiments, the single spotlights of the dissolved light system respectively have one light source and a large mirror lamp that includes one single operated light source in the lamp body.

The lamp body 2 is provided with a handle 6 protruding from the lower side of the central module 10 along a light emitting surface. The handle 6 can also be provided at another location on the lamp body 2 or on the suspension device 4.

The surgical lamp 1 further includes a focusing device 5 and dimming device 8 that are housed in a housing of the lamp body 2. However, they can also be provided at another suitable location of the surgical lamp 1. The functions of the focusing device 5 and of the dimming device 8 will be discussed below.

Figure 2:
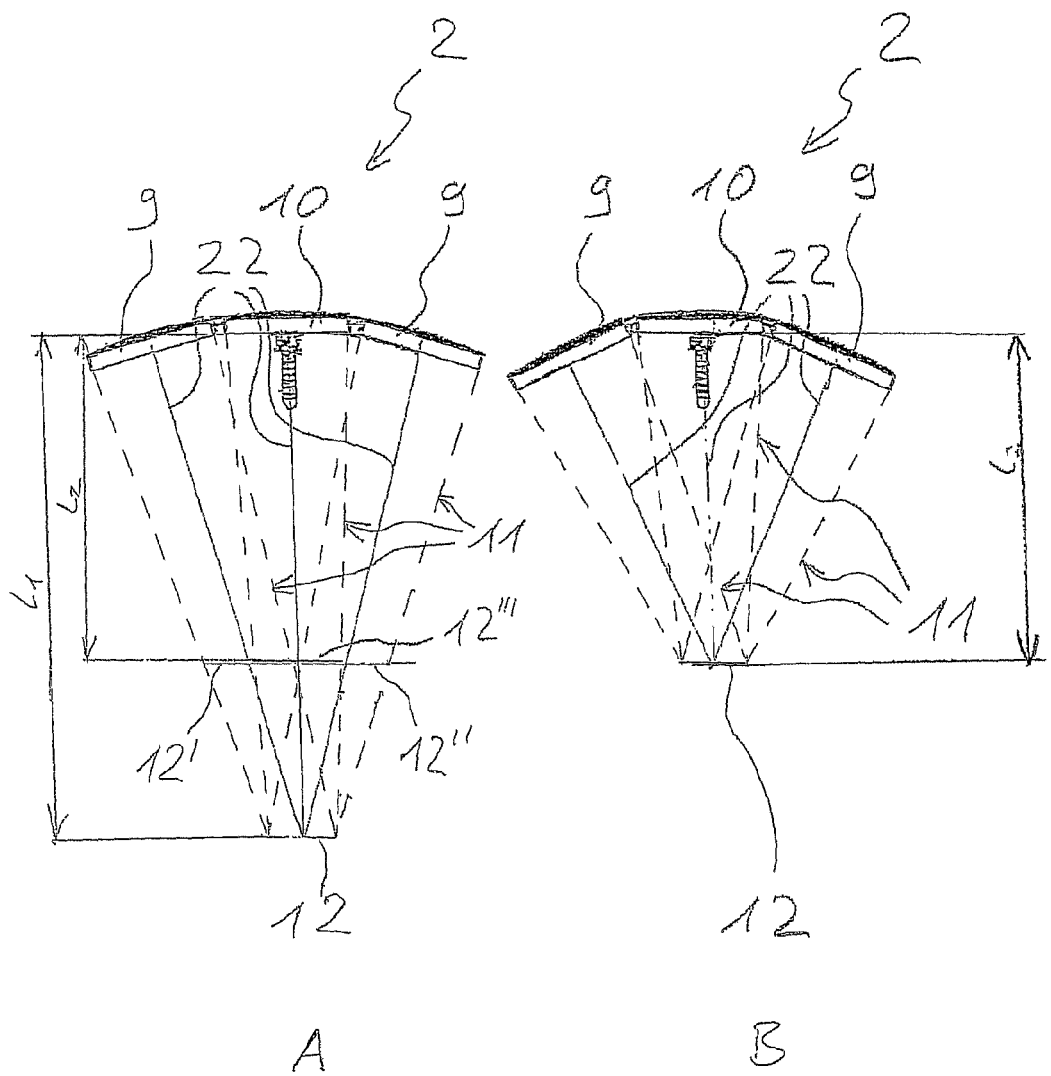
FIGS. 2A-2B respectively illustrate a lamp body of the surgical lamp of FIG. 1 emitting light under two different focus settings.

FIGS. 2A and 2B show the lamp body 2 in two different focusing settings, respectively. The edge modules 9 and the central module 10 respectively emit a bundle of light 11 which is generated by the several light sources 3. The bundles of light 11 are adapted such that each single module generates a light field (i.e., an illuminated area) on the operation site of a patient. When the focus of the bundles of light 11 is appropriate (i.e., when the angle between the respective edge module 9 and the central module 10 is chosen such that the several light fields are aligned on the operation site) a common light field 12 is generated on the operation site. The bundles of light 11 respectively include a central axis 22 intersecting on the illuminated area on the operation site when the common light field 12 is generated. In FIG. 2A, the central axes 22 of the bundles of light 11 intersect at a distance L1 from the lamp body 2. With this setting, the illumination image produced by each of the bundles of light 11 on the operation site are substantially the same, and the common light field 12 is generated. At a distance L2 of the operation field from the lamp body 2, the bundles of light 11 respectively produce light fields 12', 12", 12"' that do not intersect, but instead only overlap when the angle setting of the edge modules 9 to the central module 10 is identical.

In order to align the light fields 12', 12" and 12"' so that they are directed to the same location on the operation site at the distance L2 from the lamp body 2, the bundles of light 11 emitted from the lamp body 2 are focused in the manner shown in FIG. 2B. As shown in FIG. 2B, the edge modules 9 are pivoted inward with respect to the central module 10 such that the central axes 22 of the bundles of light 11 intersect on the operation site at the distance L2 so that the bundles of light 11 are focused on the operation field to produce the common light field 12 and optimally illuminate the operation field.

To focus the bundles of light 11, the edge modules 9 are pivoted by a drive device. The drive device is controlled by the focusing device 5 (shown in FIG. 1) according to an input of an operator. An adjustment of the angle of the edge modules 9 with respect to the central module 10 can be achieved in a substantially stepless manner between two end positions. The edge modules 9 are simultaneously adjusted so that the intersecting point of the central axes 22 of the bundles of light 11 is located along the central axis 22 of the bundle of light 11 produced by the central module 10 and the intersecting point is located at another distance away from the lamp body 2.

In some embodiments, the adjustment of the distance between the lamp body 2 and the light field 12 generated by the focused intersecting bundles of light 11 is performed in a similar way by adjusting the irradiation direction of modules or single spot lights which are provided within the lamp body of the dissolved lighting system. In the case of large mirror lamps with one illuminant and one reflector, the distance can be adjusted by displacing the illuminant along the axis of symmetry of the reflector around the focus point of the reflector.

Figure 3:
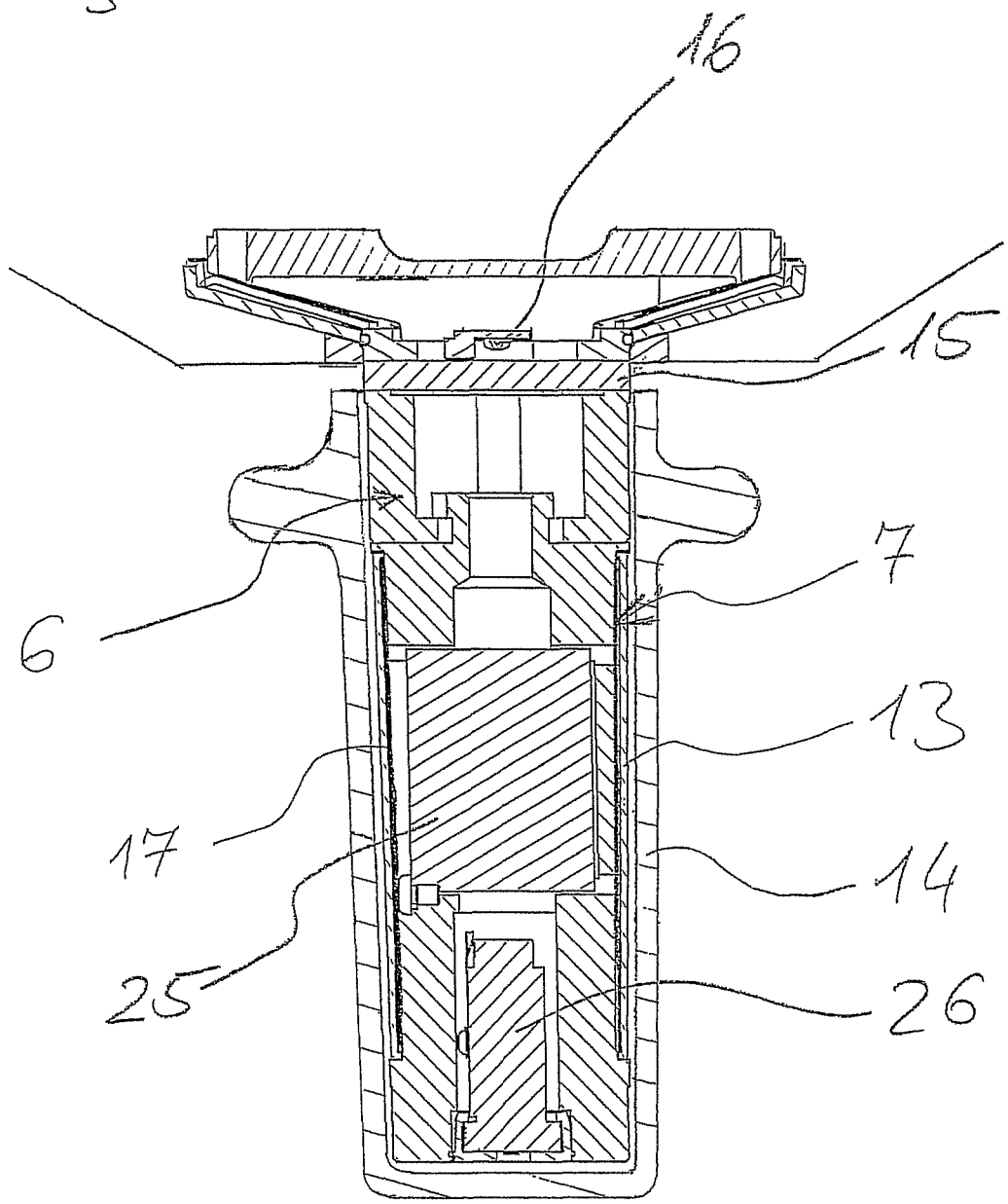
FIG. 3 is a cross-sectional view of a handle of the surgical lamp of FIG. 1 having a handle cover disposed thereon.

FIG. 3 shows the handle 6 with a handle cover 14 arranged around the handle 6. The handle 6 includes an operating device 7 that includes an operating foil 17. The handle 6 includes a circumferential recess that is a determined length along the axial direction. Into this recess, the operating foil 17 is inlaid, the length of which approximately corresponds to the length of the recess in the axial direction of the handle 6 but it is slightly shorter. The operating foil 17 has a width that approximately corresponds to the circumference of the recess in the handle 6 so that the entire circumference of the recess is covered by the operating foil 17. Around the operating foil 17, a protection cover 13 made from a rubber material is positioned. The ends of the protection cover 13 respectively form collars pointing inwardly so that the operating foil 17 can be fitted in the space axially extending between the collars. As a result of this arrangement, the operating foil 17 can be protected from humidity and mechanical damage.

The handle 6 is fixed to the lamp body 2 (shown in FIG. 1). Around the handle 6, the handle cover 14 is pushed on and it is radially and axially fixed by a snap-in element. The handle cover 14 is made of a sterilizable material in order to fulfill the hygienic requirements of a sterile operating element.

In some embodiments, the handle cover may alternatively or additionally be a disposable handle cover in the form of a sterile elastic plastic cover.

In the handle 6, an evaluation unit 25 of the operating device 7 and a laser sensor 26 for measuring distance are arranged. In some embodiments, these elements may also be arranged at other locations along the lamp body 2 or of the surgical lamp 1.

At the upper end above the handle cover 14, the operating handle 6 includes a transparent cover 15 to be a diffusing panel and an illuminant 16 to be an indicator. As described below, the illuminant 16 indicates adjusting situations of the surgical lamp 1.

The transparent cover 15 is circumferentially made of a transparent material so that the indication of the illuminant 16 can be observed from each direction around the surgical lamp.

Figure 4:
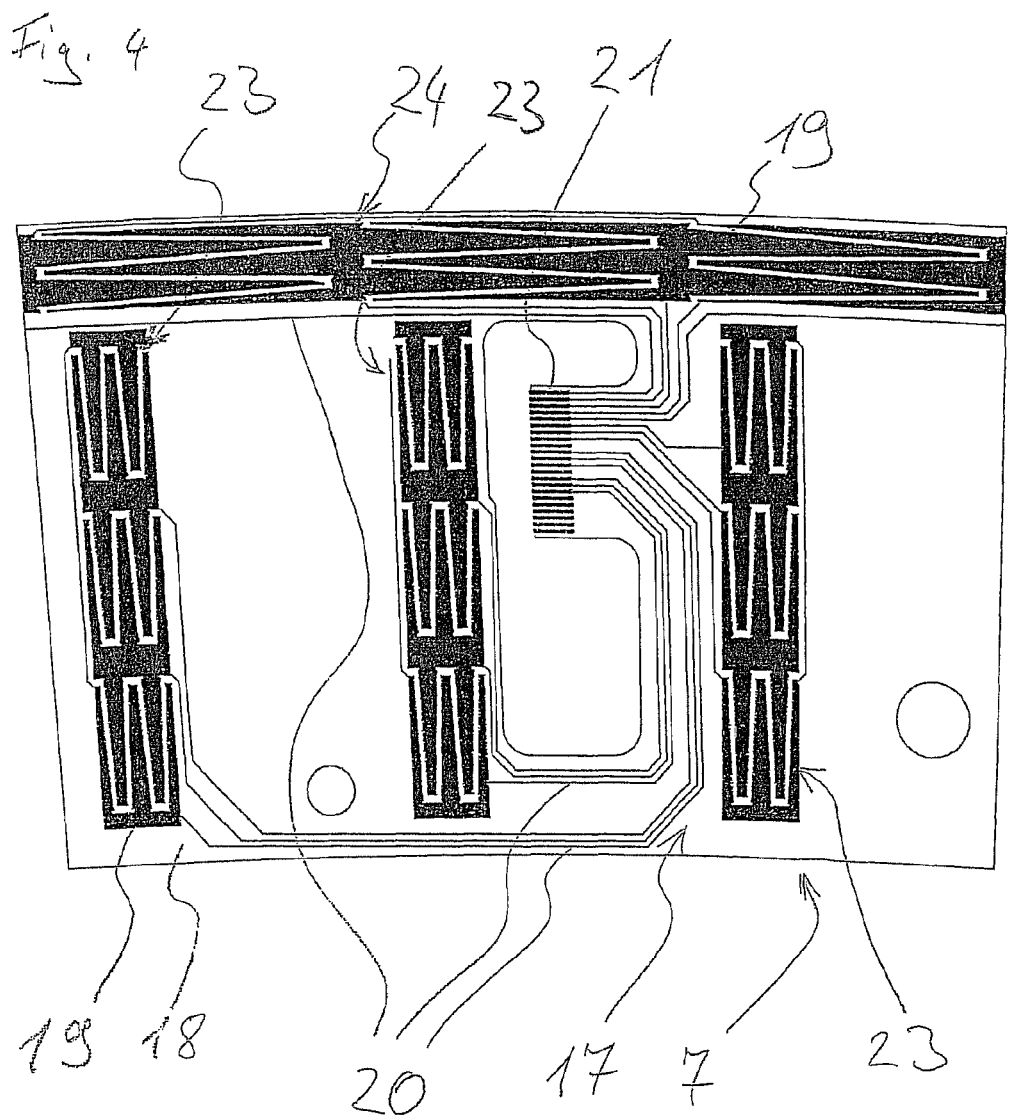
FIG. 4 illustrates an operating foil of an operating device of the surgical lamp of FIG. 1.

FIG. 4 shows the operating foil 17 of the operating device 7. As already explained in the description of FIG. 3, the operating foil 17 has a width approximately corresponding to the circumference of the recess of the handle 6. As the handle 6 is not cylindrical but slightly tapered, where the width of the operating foil 17 tapers slightly downwardly. The operating foil 17 includes a carrier foil 18 on which copper webs 19 are formed.

On the operating foil 17, four arrangements of the copper webs 19 are shown. Three arrangements of the copper webs extend in a vertical direction and respectively form a vertical sensor 23, and one arrangement of the copper webs extends in a horizontal direction at the upper end of the operating foil 17 to form a horizontal sensor 24. The copper webs 19 are respectively connected to a connector 21 via strip conductors 20. Using the connector 21, the operating foil 17 is connected to the evaluation unit 25 of the operating device 7. The evaluation unit 25 can be formed as a separate unit or, alternatively, it can be integrated in a control device of the surgical lamp 1.

In a mounted condition, the horizontal sensor 24 forms a circumferential sensor area around the handle 6. Viewed in the axial direction of the handle 6, the vertical sensors 23 respectively form a sensor area in the axial direction of the handle 6. These sensor areas are spaced apart by an angular distance of about 120°.

The copper webs 19 respectively form capacitive sensors due to their shape and their arrangement with respect to each other. In some embodiments, other operating devices that are operable in a contactless manner, such as optical operating devices, can be used.

The surgical lamp 1 is configured such that the horizontal sensor 24 is used for dimming the light sources 3 and the three vertical sensors 23 are used for the focusing the surgical lamp 1 by respectively operating the sensors 23, 24 in a contactless manner by a predetermined motion sequence of an operator.

The operating device 7 is configured such that for a control of the dimming (i.e., an alteration of illumination intensity), the horizontal sensor 24 detects when an object (e.g., a finger or a portion of a surgical instrument) is brought into the region of the horizontal sensor 24. Thereby, the horizontal sensor 24 outputs a corresponding signal to the evaluation unit 25 whereby the operating device 7 recognizes the insertion of the object into the region of the horizontal sensor 24. By moving the object along the circumference of the handle 6 or of the mounted handle cover 14 (i.e., along the horizontal sensor 24), the horizontal sensor 24 detects the position of the object, by the movement with respect to the initially detected position, and the horizontal sensor 24 transmits corresponding signals to the evaluation unit 25. The operating unit 7 is configured such that the evaluation unit 25 recognizes which direction the object is moved, in particular, clockwise or counter-clockwise with respect to the axis of the handle 6. The evaluation unit 25 then recognizes the distance that the object is moved. Furthermore, the operating device 7 is configured such that its evaluation unit 25 outputs respective signals corresponding to the direction of the movement and the distance of the movement of the object to the dimming device 8. A direction of the movement that is clockwise with respect to the axial direction of the handle 6 corresponds to an increase of the brightness of the surgical lamp 1 and a movement which is counterclockwise corresponds to a decrease of the brightness. In some embodiments, this correlation may be different.

In certain embodiments, the evaluation unit 25 is configured such that a distance of the object of 1 cm along the horizontal sensor 24 corresponds to the change of one brightness level. The change of the light intensity per brightness level is defined in the dimming device 8. In some embodiments, the correlation of the distance and a brightness level may correspond to different value or it may be stepless.

The operating device 7 is configured such that for controlling the focusing, one or more of the vertical sensors 23 recognize when an object (e.g., a finger or a portion of a surgical instrument) is brought into the region of one of the vertical sensors 23 and then outputs a corresponding signal to the evaluation unit 25, whereby, the operating device 7 recognizes the insertion of the object into the region of the vertical sensors 23. By moving the object along the handle 6 in the axial direction (i.e., along the vertical sensors 23), the vertical sensors 23 transmit signals to the evaluation unit 25 based on the position of the object with respect to its initial position. The operating device 7 is configured such that it also recognizes which direction the object is moved, in particular, towards the lamp body 2 or away from the lamp body 2. When the object is moved away from the lamp body 2, the evaluation unit 25 of the operating device 7 outputs a signal to the focusing device 5 to move the edge modules 9 inward (i.e., to reduce the distance between the point in which the axes 22 of the bundles of light 11 are focused and the lamp body 2). A movement of the object towards the lamp body 2 results in an output of signals of the operating device 7 to the focusing device 5 for moving the edge modules 9 apart (i.e., the distance between the intersecting point of the axes 22 of the bundles of light 11 and the lamp body 2 is increased).

In other embodiments, the evaluation unit 25 of the operating device 7 outputs a signal to the focusing device 5 to move the edge modules 9 inward when the object is moved toward the lamp body 2 and to move the edge modules 9 outward when the object is moved away from the lamp body 2.

The signal for focusing the light is output as long as the evaluation unit 25 detects the presence of the object in the region of one of the vertical sensors 23 during or after the movement until the object is removed from the sensor area. When the direction of movement of the object is reversed without removing the object from the sensor region, a signal to change the distance between the intersecting point of the axes 22 and the lamp body 2 into the reverse direction is provided to the focusing device 5 until the object is removed from the sensor area.

Typically, the surgical lamp 1 is in an automatic mode in which the distance between the lamp body 2 and the operation site is measured by a distance measurement using the laser sensor 26. Thereby, the optimum light field 12 is adjusted by the focusing device 5. The surgeon can typically correct the automatic adjustment by adjusting the operating device 7. Alternatively, when the automatic function is missing when the surgical lamp 1 is turned on, the last set distance may be maintained or a value predetermined as standard distance (e.g., a standard value of one meter) can be adjusted.

The operating device 7 is connected to the control device of the surgical lamp 1 which, in turn, is connected to the focusing device 5 and the dimming device 8 so that it can control them. In some embodiments, the operating device 7 is directly connected to the focusing device 5 and to the dimming device 8.

In some embodiments, the correlation between the vertical sensors 23 and the horizontal sensors 24 and the functions of dimming and focusing light can be determined in a different way. Also, the detection of the direction of the movement and the duration of the presence of the object is not restricted to a certain sensor or to a certain function, but the correlation can be performed in any of various arbitrary suitable manners. Also, in some embodiments, the control of other functions (e.g., an adjustment of the color temperature of emitted light) is possible. Furthermore, in some embodiments, the detection of other motion sequences, such as, for example, tapping a finger or combinations of motion sequences (e.g., overlaying the vertical sensors 23 and the horizontal sensor 24 to detect movements that are diagonal with respect to the axial direction of the handle 6) is possible.

By the contactless detection, the operator (e.g., a surgeon) may either operate the appropriate functions of the surgical lamp 1 without actually touching the surgical lamp 1 or by moving the object along a sterilizable cover (e.g., the sterile handle cover 14), which enables the sterile operation of the surgical lamp 1.

The sensitivity of the capacitive sensors is typically adjustable or programmable by a device for adjusting the evaluation unit 25 of the operating device 7. A calibration device that automatically calibrates the operating device 7 during power-up is provided to detect which evaluation unit input values are present during power-up in order to provide a safe and accurate detection of the object. These values are set to be limit values of a "non-operation" so that the approach and movement of an object (e.g. the finger) is recognized. Thus, control of the focusing or the dimming is also performed without the handle cover, with an arbitrary handle cover, or with the elastic plastic cover. The detected values are periodically reviewed to determine whether prolonged modifications of the values appear. Thereby, the pushing on and mounting of a handle cover 14 which has not been mounted during power-up of the surgical lamp 1 (i.e., which has not undergone calibration) is recognized and the values are adjusted so that a detection of an object (e.g., a finger) is achieved despite the pushed-on handle cover 14.

In order to reduce (e.g., minimize) the likelihood of an unintentional operation of the operating device 7, several techniques can be implemented.

In some embodiments, repositioning the lamp body 2 of the surgical lamp 1 is recognized by an acceleration sensor that is provided in the lamp body 2 and is connected to the control device of the surgical lamp 1. The operating device 7 is configured to be directly controlled by a control device of the surgical lamp 1 or alternatively by the acceleration sensor so that it does not react to the signals produced by the vertical sensors 23 and/or horizontal sensor 24 during repositioning so that no signals are passed to the focusing device 5 and/or dimming device 8.

In another approach for preventing unintentional operation of the operating device 7, focusing of the bundles of light 11 or dimming of the brightness only starts when an object is recognized at the handle 6 and moved along a certain distance (e.g., 1 cm). When operating the surgical lamp 1 in this manner, detection of only a mere presence of the object (e.g., as a result of gripping the handle cover 14 for repositioning) is not detected to be an operation for altering the light emitted from the surgical lamp 1.

The illuminant 16 is used for indicating an alteration of adjustments of the surgical lamp 1. The illuminant 16 is operated in a basic brightness at a medium brightness level. When altering one of the adjustable settings of the surgical lamp 1 (e.g., dimming or focusing the emitted light), such altering is indicated by changes in the brightness of the indicator illuminant 16. By controlling the dimming device 8 in order to increase the luminosity of the surgical lamp 1, the brightness of the indicator illuminant is also increased. An alteration of the focusing is also indicated by increased brightness of the indicator illuminant when the edge modules 9 are moved together. Similarly, when the brightness of the surgical lamp 1 is decreased or when the edge modules 9 are moved apart, the brightness of the indicator illuminant 16 decreases. After the adjustment process initiated by the operating device 7 is complete, the indicator illuminant 16 is reset to the basic brightness level by a control unit to which it is connected.

The indicator illuminant 16 is typically in the form of an LED. Alternatively, a scale having multiple LEDs is also possible. Furthermore, it is alternatively possible to activate the indicator illuminant 16 according to the actually altered function of the surgical lamp 1 and to indicate the actual setting. Alternatively, the constant indication of a setting, such as the focus of the surgical lamp 1 is possible. Moreover, an acoustical feedback to indicate brightness or focus adjustments is also possible.

The number of the sensors 23, 24 depends on the number of the functions to be adjusted. For an ergonomic operation of the surgical lamp, multiple sensors 23, 24 for one function may also be provided at different locations of the surgical lamp or one sensor may be provided at a desired location of the surgical lamp. However, the sensors are actuated through a sterilizable cover, such as the handle cover 14, covering the sensor.

A number of embodiments of the invention have been described. Nevertheless, it will be understood that various modifications may be made without departing from the spirit and scope of the invention. Accordingly, other embodiments are within the scope of the following claims.

What is claimed is:

1. A surgical lamp comprising:
   a lamp body comprising a plurality of light sources, each light source of the plurality of light sources being configured to emit at least one bundle of light;
   a focusing device disposed in the lamp body for aligning the at least one bundle of light emitted from a first light source of the plurality of light sources with the at least one bundle of light emitted from a second light source of the plurality of light sources; and
   an operating device that is directly or indirectly connected to the focusing device; and
   a sterilizable cover that covers the operating device,
   wherein the operating device is configured to detect a motion sequence of an operator in a contactless manner and to control the focusing device based on the detected motion sequence.

2. The surgical lamp according to claim 1, further comprising:
   a suspension device to which the lamp body is attached; and
   a handle attached to the suspension device or to the lamp body, the sterilizable cover being configured to receive the handle,
   wherein the operating device is disposed on the handle.

3. The surgical lamp according to claim 1, further comprising a dimming device for the plurality of light sources, wherein the operating device is directly or indirectly connected to the dimming device so that an operation of the operating device by the motion sequence of the operator controls dimming of the light source.

4. The surgical lamp according to claim 3, wherein the operating device is configured to detect different motion sequences of the operator that correspond to different settings of the focusing device and the dimming device, and to submit a control signal to the focusing device or to the dimming device in response to detecting the different motion sequences.

5. The surgical lamp according to claim 4, wherein the operating device is configured so that a first motion sequence for controlling the focusing device is different from a second motion sequence for controlling the dimming device.

6. The surgical lamp according to claim 4, wherein the operating device is configured to detect different respective directions of the motion sequences and to transmit respective control signals to the focusing device or to the dimming device based on the detected respective directions of the motion sequences.

7. The surgical lamp according to claim 6, wherein the lamp body comprises an illuminant indicator device that is configured so that, beginning from a basic brightness, the illuminant indicator device becomes lighter or darker depending on the direction of the motion sequence.

8. The surgical lamp according to claim 7, wherein the illuminant indicator device is connected to a control unit that is configured so that after termination of the motion sequence, the indicator device is reset to the basic brightness.

9. The surgical lamp according to claim 1, wherein the operating device comprises a device for adjusting a sensitivity of the detection of the motion sequence of the operator in a contactless manner.

10. The surgical lamp according to claim 9, wherein the operating device comprises a device for calibrating the sensitivity of the detection of the motion sequence of the operator in a contactless manner.

11. The surgical lamp according to claim 1, wherein the surgical lamp comprises an acceleration sensor which is directly or indirectly connected to the operating device, and the surgical lamp is configured so that the focusing device is not actuated when a motion sensor detects a movement of the lamp body.

12. The surgical lamp according to claim 1, wherein the operating device comprises at least one capacitive sensor.

13. The surgical lamp according to claim 1, wherein the operating device is configured so that the detection of the motion sequence of the operator is possible with and without the sterilizable cover disposed on the operating device.

14. A method for controlling a surgical lamp, the method comprising:

detecting, using an operating device, an insertion of an object into a region of a sensor;

determining a first position of the object;

detecting, using the operating device, a second position of the object with respect to the first position;

determining a distance that the object has moved between the first position and the second position;

outputting a signal from the operating device according to a direction of movement of the object and the distance that the object has moved; and aligning, using a focusing device, a first bundle of light emitted from the surgical lamp with a second bundle of light emitted from the surgical lamp based on the signal output from the operating device.

15. The method according to claim 14, wherein when the object is moved in a first direction, the signal output from the operating device causes a brightness emitted by light modules of the surgical lamp to increase, and when the object is moved in a second opposite direction, the signal output from the operating device causes the brightness emitted by the light modules to decrease.

16. The method according to claim 14, wherein when the object is moved in a first direction, the signal output from the operating device causes a focus point of light emitted by light modules of the surgical lamp to move away from the surgical lamp, and when the object is moved in a second opposite direction, the signal output from the operating device causes the focus point of light emitted by the light modules to move toward the surgical lamp.

17. A method for controlling a surgical lamp, the method comprising:

detecting, using an operating device, an insertion of an object into a region of a sensor;

determining a first position of the object;

detecting, using the operating device, a direction in which the object moves with respect to the first position;

outputting a signal from the operating device according to the detected direction of movement of the object; and performing a function based on the signal output by the operating device as long as the operating device detects the presence of the object, the function comprising at least aligning, using a focusing device, a first bundle of light emitted from the surgical lamp with a second bundle of light emitted from the surgical lamp to adjust a focus position of light emitted from the surgical lamp.

18. The method according to claim 17, wherein the function further comprises adjusting a brightness of light emitted from the surgical lamp.

19. The method according to claim 17, wherein the focus position of light emitted from the surgical lamp is adjusted when the direction is substantially parallel to a central axis of the surgical lamp.

20. The method according to claim 18, wherein the brightness of light emitted from the surgical lamp is adjusted when the direction is substantially transverse to a central axis of the surgical lamp.

* * * * *